United States Patent [19]

Beeley et al.

[11] Patent Number: 5,750,701
[45] Date of Patent: May 12, 1998

[54] HETEROCYCLIC ETHANOLAMINE DERIVATIVES WITH β-ADRENORECEPTOR AGONISTIC ACTIVITY

[75] Inventors: Lee James Beeley; David Kenneth Dean, both of Dorking, United Kingdom

[73] Assignee: SmithKline Beecham plc, Brentford, United Kingdom

[21] Appl. No.: 704,699

[22] PCT Filed: Mar. 3, 1995

[86] PCT No.: PCT/EP95/00794

§ 371 Date: Sep. 16, 1996

§ 102(e) Date: Sep. 16, 1996

[87] PCT Pub. No.: WO95/25104

PCT Pub. Date: Sep. 21, 1995

[30] Foreign Application Priority Data

Mar. 15, 1994 [GB] United Kingdom ............ 9405019

[51] Int. Cl.$^6$ ............ C07D 215/227; C07D 215/36; A61K 31/47
[52] U.S. Cl. ............ 546/157; 514/312; 514/398; 514/82; 514/367; 514/376; 514/397; 514/305.1; 546/156; 546/23; 548/306.4; 548/307.1; 548/221; 548/169; 548/305.1
[58] Field of Search ............ 546/157; 514/312

[56] References Cited

U.S. PATENT DOCUMENTS

| 4,579,854 | 4/1986 | Iwakuma et al. | 514/312 |
| 4,810,712 | 3/1989 | Cohnen et al. | 514/312 |
| 4,894,219 | 1/1990 | Baker et al. | 424/9 |

FOREIGN PATENT DOCUMENTS 0 147 719 10/1985 European Pat. Off.

OTHER PUBLICATIONS

Milecki, J. et al. J. Med. Chem. vol. 30 No. 9, Sep. 1987, pp. 1563–1566 Carbostyril derivatives haaving a . . .

Primary Examiner—Mukund J. Shah
Assistant Examiner—King Lit Wong
Attorney, Agent, or Firm—Charles M. Kinzig; Edward T. Lentz

[57] ABSTRACT

A compound of the formula (I), or a pharmaceutically acceptable salt thereof, or a pharmaceutically acceptable solvate thereof, wherein, X represents a moiety of formula (a), in which $A^1$ represents —CH=CH=, NH, S or O; $A^2$ represents an oxo or a thioxo group; $A^3$ represents H or an alkylcarbonyl group; and $A^4$ represents hydroxy or NR$^s$R$^t$ wherein R$^s$ and R$^t$ each independently represents H or alkyl; $R^0$ and $R^1$ each independently represents hydrogen or an alkyl group; $R^2$ represents OCH$_2$CO$_2$H, or an ester or amide thereof, or $R^2$ represents a moiety of formula (b), wherein $R^4$ and $R^5$ each independently represent hydrogen, alkyl, hydroxyalkyl, cycloalkyl or $R^4$ together with $R^5$ represents (CH$_2$)$_n$ wherein n is 2, 3 or 4; and $R^3$ represents hydrogen, halogen, alkyl or alkoxy or $R^3$ together with $R^2$ represents a moiety of formula (c) or an ester or amide thereof, wherein R represents hydrogen, alkyl, hydroxymethyl or a moiety of formula (CH$_2$)$_n$CO$_2$H, wherein n is zero or an integer 1, 2 or 3, or an ester or amide thereof; a process for the preparation of such a compound, a pharmaceutical composition containing such a compound and the use of such a compound and composition in medicine.

13 Claims, No Drawings

HETEROCYCLIC ETHANOLAMINE DERIVATIVES WITH β-ADRENORECEPTOR AGONISTIC ACTIVITY

This is a 371 application of PCT/EP95/00794, filed Mar. 3, 1995.

This invention relates to novel compounds, to a process for preparing such compounds, to pharmaceutical compositions containing such compounds and to the use of such compounds and compositions in medicine and agriculture.

It has been discovered that a series of novel heterocyclic ethanolamine derivatives have good β-adrenoreceptor agonist activity and in particular show good selectivity for $β_3$-adrenoreceptors versus $β_1$- or $β_2$-adrenoreceptors. These compounds are therefore indicated to have good anti-hyperglycaemic and/or anti-obesity activity coupled with especially good selectivity from cardiac and tremorigenic side effects.

These compounds are also indicated to have potential in the treatment of gastrointestinal disorders such as peptic ulceration, oesophagitis, gastritis and duodenitis, intestinal ulcerations, including inflammatory bowel disease, and irritable bowel syndrome and also for the treatment of gastrointestinal ulcerations, especially when induced by non-steroidal anti-inflammatory drugs or corticosteroids.

These compounds also have potential as growth promoters for livestock and for decreasing birth mortality rate and increasing the post-natal survival rate in livestock. These compounds may also be of use in increasing the high-density-lipoprotein (HDL) cholesterol concentration and decreasing the triglyceride concentration in human blood serum and are therefore of potential use in the treatment and/or prophylaxis of atherosclerosis. They are also indicated to be useful for the treatment of hyperinsulinaemia. They are also indicated to be useful for the treatment of depression.

Accordingly the present invention provides a compound of formula (I):

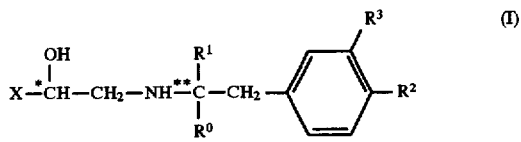

or a pharmaceutically acceptable salt thereof, or a pharmaceutically acceptable solvate thereof, wherein, X represents a moiety of formula (a):

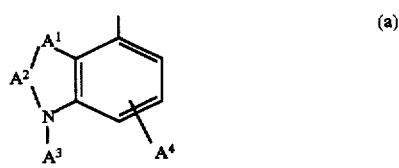

in which $A^1$ represents —CH=CH—, NH, S or O; $A^2$ represents an oxo or a thioxo group; $A^3$ represents H or an alkylcarbonyl group; and $A^4$ represents hydroxy or $NR^rR^{r'}$ wherein $R^r$ and $R^{r'}$ each independently represents H or alkyl; $R^0$ and $R^1$ each independently represents hydrogen or an alkyl group;

$R^2$ represents $OCH_2CO_2H$, or an ester or amide thereof, or $R^2$ represents a moiety of formula (b):

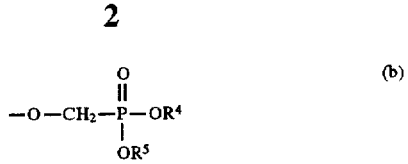

wherein $R^4$ and $R^5$ each independently represent hydrogen, alkyl, hydroxyalkyl, cycloalkyl or $R^4$ together with $R^5$ represents $(CH_2)_m$ wherein m is 2, 3 or 4; and $R^3$ represents hydrogen, halogen, alkyl or alkoxy or $R^3$ together with $R^2$ represents a moiety of formula (c):

or an ester or amide thereof, wherein R represents hydrogen, alkyl, hydroxymethyl or a moiety of formula $(CH_2)_nCO_2H$, wherein n is zero or an integer 1, 2 or 3, or an ester or amide thereof.

Suitably, $A^1$ is —CH=CH—.
Suitably, $A^2$ is oxo.
Suitably, $A^3$ is H.
Suitably, $A^4$ is OH, favourably substituted at the 4-position relative to the bond linking X to the CHOH carbon atom.
Suitably $R^0$ is hydrogen.
Suitably, $R^1$ is an alkyl group.
When $R^1$ is alkyl, it is favourably a $C_{1-6}$ alkyl group, especially a methyl group.
Suitably, $R^2$ together with $R^3$ represents a moiety of formula (c).

The compounds of formula (I) have two or more asymmetric carbon atoms, for example those marked with asterisks in the formula. These compounds may therefore exist in different stereoisomeric forms. The present invention encompasses all stereoisomers of the compounds of the general formula (I) whether free from other isomers, or admixed with other isomers in any proportion, such as mixtures of diastereoisomers and racemic mixtures of enantiomers.

Of particular interest are those carbon atoms marked with one (*) or two (**) asterisks in the formula.

Preferably, the asymmetric carbon atom indicated by a single asterisk (*) is in the R-configuration.

Preferably, the asymmetric carbon atom indicated by two asterisks (**) is in the R-configuration.

It should also be mentioned that the carbon atom in moiety (c) marked with three asterisks (***) may also be chiral when R is different from the other attached substituent (as selected from $CO_2H$ or an ester or amide thereof).

When the (***) carbon is non-chiral, a suitable form of a compound of formula (I) is a mixture of the R(*)R(**) and S(*)S(**) enantiomers.

When the (***) carbon is non-chiral, a preferred form of a compound of formula (I) is the R(*)R(**) enantiomer.

The term 'alkyl' when used alone or when forming part of other groups (such as the 'alkoxy' group) includes straight- or branched-chain alkyl groups containing 1 to 12 carbon atoms, suitably 1 to 6 carbon atoms, examples include methyl, ethyl, n-propyl, isopropyl, n-butyl, isobutyl or tert-butyl group.

The term 'cycloalkyl' includes $C_{3-8}$ cycloalkyl groups, especially $C_5$ or $C_6$ cycloalkyl groups.

When used herein the term "halogen" refers to fluorine, chlorine, bromine and iodine, preferably chlorine.

Suitable esters are pharmaceutically acceptable esters.

Suitable pharmaceutically acceptable esters of carboxyl groups include alkyl esters, especially $C_{1-6}$ alkyl esters such as methyl.

Suitable amides are pharmaceutically acceptable amides.

Suitable pharmaceutically acceptable amides are those of formula —CONR$^j$R$^k$ wherein R$^j$ and R$^k$ each independently represent hydrogen, alkyl or alkoxyalkyl.

Suitable salts are pharmaceutically acceptable salts.

Suitable pharmaceutically acceptable salts include acid addition salts, salts of carboxy groups and salts of phosphonic acid groups.

Suitable pharmaceutically acceptable acid addition salts include salts with inorganic acids such, for example, as hydrochloric acid, hydrobromic acid, orthophosphoric acid or sulphuric acid, or with organic acids such, for example as methanesulphonic acid, toluenesulphonic acid, acetic acid, propionic acid, lactic acid, citric acid, fumaric acid, malic acid, succinic acid, salicylic acid, maleic acid or acetylsalicylic acid.

Suitable pharmaceutically acceptable salts of carboxy groups or phosphonic acid groups include metal salts, such as for example aluminium, alkali metal salts such as lithium, sodium or potassium, alkaline earth metal salts such as calcium or magnesium and ammonium or substituted ammonium salts, for example those with $C_{1-6}$ alkylamines such as triethylamine, hydroxy-$C_{1-6}$ alkylamines such as 2-hydroxyethylamine, bis-(2-hydroxyethyl)-amine or tri-(2-hydroxyethyl)-amine, cycloalkylamines such as bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as pyridine, collidine or quinoline.

Suitable solvates are pharmaceutically acceptable solvates.

Suitable pharmaceutically acceptable solvates are conventional solvates, preferably hydrates.

The invention also provides a process for the preparation of a compound of formula (I), or a pharmaceutically acceptable salt thereof, or a pharmaceutically acceptable solvate thereof, which process comprises reacting a compound of formula (II):

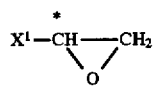
(II)

wherein $X^1$ represents X as defined in relation to formula (I) or a protected form thereof, with a compound of formula (III):

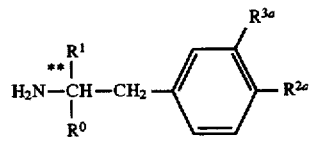
(III)

wherein $R^0$, $R^1$ are as defined in relation to formula (I), $R^{2a}$ represents $R^2$ as defined in relation to formula (I) or a protected form thereof and $R^{3a}$ represents $R^3$ as defined in relation to formula (I) or a protected form thereof; and thereafter, if necessary, carrying out one or more of the following optional steps:

(i) converting one compound of formula (I) into another compound of formula (I);

(ii) removing any protecting group; and (ii) preparing a pharmaceutically acceptable acid addition salt of a compound of formula (I) or a pharmaceutically acceptable solvate thereof.

The reaction between the compounds of formulae (II) and (III) may be carried out in any suitable solvent, generally being an alkanol such as ethanol, at any temperature providing a suitable rate of formation of the required product, suitably at an elevated temperature, such as the reflux temperature of the solvent and preferably under an inert atmosphere such as argon or nitrogen.

The compounds of formulae (II) are known compounds or they may be prepared using processes analogous to those used to prepare such compounds, for example by use of the methods or analogous methods to those disclosed in Journal of Medical Chemistry 1987, 30, 1563–1566.

A chiral compound of formula (II) wherein the C* carbon atom is chiral may be prepared from an activated form of a compound of formula (IV):

(IV)

wherein $X^1$ is as defined in relation to formula (II), C* is a chiral carbon and $L^1$ is a leaving group or atom, usually a halogen atom such as a chlorine atom, by an intramolecular displacement reaction.

A suitable activated form of a compound of formula (IV) is a salted form such as an alkali metal salted form, suitably a potassium salted form.

The activated form of a compound of formula (IV) may be prepared by the appropriate conventional process depending upon the particular nature of the activated form, for example when the activated form is a salted form the compound of formula (IV) is treated with an appropriate source of salting ion such as an alkali metal salt; for example potassium carbonate, in any suitable aprotic solvent such as acetone.

The intramolecular displacement reaction of the activated form of the compound of formula (IV) may be carried out in any suitable aprotic solvent, such as acetone, at any temperature which provides a suitable rate of formation of the required product, usually at an elevated temperature such as the reflux temperature of the solvent.

Conveniently the activated form of the compound of formula (IV) is prepared in situ with respect to the intramolecular displacement reaction for formation of the required compounds of formula (H).

A compound of formula (IV) may be prepared by the chiral reduction of a compound of formula (V):

(V)

wherein $X^1$ and $L^1$ are as defined in relation to formula (IV).

The chiral reduction of the compound of formula (V) may conveniently be carried out using borane, suitably as a tetrahydrofuran complex, in the presence of a chiral reduction catalyst such as those disclosed in Journal of American Chemical Society 1987, 109, 5551–5553.

Suitable conditions for the reduction of the compound of formula (V) are the appropriate conventional conditions for example the borane reduction may be carried out using the conditions described in Journal of American Chemical Society, ibid.

A compound of formula (V) may be prepared by halogenating a compound of formula (VI):

(VI)

when $X^1$ is as defined above.

The halogenation of the compound of formula (VI) is conveniently carried out using a benzyltrimethylammonium dihaloiodate as a halogenating agent (for example benzyltrimethylammonium dichloroiodate is used for chlorination) under conditions disclosed in the Synthesis, 1988, 545–546.

The compounds of formula (VI) are known compounds or they may be prepared using methods analogous to those used to prepare such compounds, for example by use of the methods or analogous methods to those disclosed in the European Journal of Medicinal Chemistry, 1984, 19, 341–346.

The compounds of formula (III) are known compounds or they may be prepared according to methods used to prepare known compounds, for example by use of the methods or analogous methods to those disclosed in European Patent Application Number 0023385 (especially for compounds of formula (III) wherein $R^2$ is $OCH_2CO_2H$ or an ester or amide thereof) or International Application, Publication Number WO 94/02493 (especially for compounds wherein $R^2$ is a moiety of hereinbefore defined formula (b)).

A compound of formula (III) wherein $R^2$ and $R^3$ together represent a moiety of the above defined formula (c), may be prepared by reacting an activated form of a compound of formula (VII):

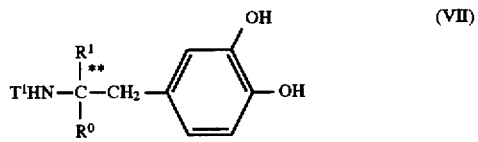

(VII)

when $R^0$ and $R^1$ are as defined in relation to formula (I) and $T^1$ is hydrogen or a nitrogen protecting group, with a compound of formula (VIII):

(VIII)

wherein $L^2$ represents a leaving group or atom, suitably a halogen group such as a bromine atom, $R^a$ represents R as defined in relation to formula (I) or a protected form thereof and $T^2$ represents hydrogen or a carboxyl protecting group; and thereafter as required, removing any protecting group.

Suitably $T^1$ is a nitrogen protecting group, such as a tert-butyloxycarbonyl group.

Suitably $T^2$ is a carboxyl protecting group, such as an alkyl group.

$R^a$ represents a protected form of R when required by the particular nature of R, for example when R is carboxyl then $R^a$ is a protected carboxyl group such as a group $CO_2T^2$ defined above.

A suitable activated form of a compound of formula (VII) is an ionic form, such as a salted form, for example an alkali metal salted form.

The activated form of a compound of formula (IV) may be prepared by the appropriate conventional process depending upon the particular nature of the activated form, for example when the activated form is a salted form the compound of formula (VII) is treated with an appropriate source of salting ion such as an alkali metal salt; for example potassium carbonate, in any suitable aprotic solvent such as acetone.

The reaction between the compounds of formulae (VII) and (VIII) may be carried out in any suitable aprotic solvent, such as acetone, at any temperature which provides a suitable rate of formation of the required product, usually at an elevated temperature such as the reflux temperature of the solvent.

Conveniently the activated form of the compound of formula (VII) is prepared in situ with respect to the reaction between the compounds of formulae (VII) and (VIII) which then form the required compounds of formula (III).

A compound of formula (VII) is conveniently prepared according to the reaction scheme set out below:

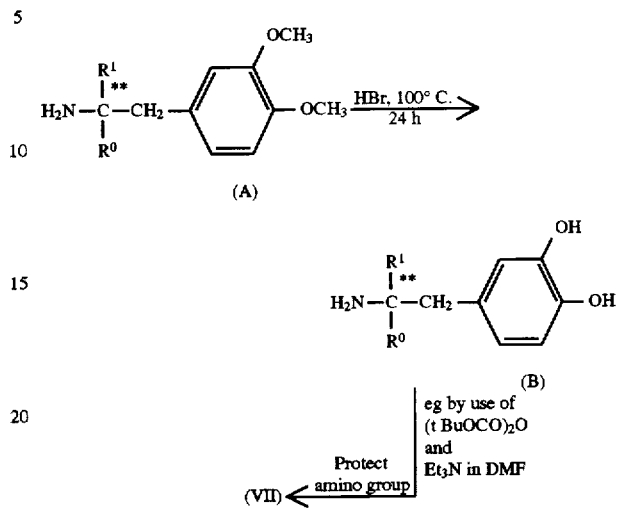

The conditions of reaction for the above reaction scheme are those used conventionally in the art such as the conditions described in the accompanying examples.

Suitably the C* and C** carbon atom are chiral carbon atoms.

The compounds of formulae (VIII) are either known commercially available compounds (for example, the compounds wherein R is $CO_2H$) or an ester or amide thereof or they may be prepared from such compounds using routine procedures or they may be prepared using methods or analogous methods to those used to prepare known compounds, for example those disclosed in Bull. Korean Chem. Soc. 1992, 13, 226–227.

The compounds of formulae (A) are known compounds or they may be prepared by processes analogous to those used to prepare known compounds, for example by use of the methods or analogous methods disclosed in the Journal of Medicinal Chemistry 1973, 16, 480–483.

Suitable conversions of one compound of formula (I) into another compound of formula (I) include converting one group $OR^4$ into another group $OR^4$ and/or converting one group $OR^5$ into another group $OR^5$.

Suitable conversions of one group $OR^4$ into another group $OR^4$ include:

(i) converting $OR^4$ as hydroxy into $OR^4$ as alkoxy;

(ii) converting $OR^4$ as alkoxy into $OR^4$ as hydroxy;

(iii) converting $OR^4$ as alkoxy into $OR^4$ as another alkoxy group.

The abovementioned conversion (i) may be carried out under conventional phosphonate alkylation methods, using for example the appropriate alcohol ($R^4OH$) in the presence of hydrogen chloride.

The abovementioned conversion (ii) may be carried out using conventional phosphonate hydrolysis methods, for example by treating the appropriate compound of formula (I) with an alkaline metal hydroxide, such as sodium hydroxide.

The abovementioned conversion (iii) may be carried out by first converting $OR^4$ as alkoxy into $OR^4$ as hydroxy using the conditions set out in respect of the abovementioned conversion (ii), followed by converting the hydroxy group so formed into another alkoxy group, using the conditions set out in respect of the abovementioned conversion (i).

The abovementioned conversion (iii) is of particular use for preparing compounds of formula (I) wherein $OR^4$ represents methoxy: such compounds are generally prepared from compounds of formula (I) wherein $OR^4$ represents an alkyloxy group other than methoxy (suitably ethoxy) by first hydrolysing the relevant $OR^4$ group (via conversion (ii)) to prepare a compound of formula (I) wherein $OR^4$ represents hydroxy and thereafter methylating (via conversion (i)) to provide the required compound wherein $OR^4$ represents methoxy.

Suitable conversions of one group $OR^5$ into another group $OR^5$ include analogous conversions to those mentioned above in regard to converting one group $OR^4$ into another group $OR^4$.

The protection of any reactive group or atom, may be carried out at any appropriate stage in the aforementioned processes. Suitable protecting groups include those used conventionally in the art for the particular group or atom being protected. Protecting groups may be prepared and removed using the appropriate conventional procedure. For example when $T^1$ represents a tert-butyloxycarbonyl nitrogen protecting group it may be removed by acidic hydrolysis, using hydrogen chloride in ether/ethyl acetate, or when $T^2$ represents an alkyl group as a carboxyl protecting group it may be removed by catalytic hydrogenation, using a palladium on carbon catalyst.

A leaving group or atom is any group or atom that will, under the reaction conditions, cleave from the starting material, thus promoting reaction at a specified site. Suitable examples of such groups unless otherwise specified are halogen atoms, mesyloxy groups and tosyloxy groups.

The salts, esters, amides and solvates of the compounds mentioned herein may be produced by methods conventional in the art: For example, acid addition salts may be prepared by treating a compound of formula (I) with the appropriate acid.

Esters of carboxylic acids may be prepared by conventional esterification procedures, for example alkyl esters may be prepared by treating the required carboxylic acid with the appropriate alkanol, generally under acidic conditions.

Amides may be prepared using conventional amidation procedures, for example amides of formula $CONR^jR^k$ may be prepared by treating the relevant carboxylic acid with an amine of formula $HNR^jR^k$, wherein $R^j$ and $R^k$ are as defined above. Alternatively, a $C_{1-6}$ alkyl ester such as a methyl ester of the acid may be treated with an amine of the above defined formula $HNR^jR^k$ to provide the required amide.

Compounds of formula (I) and pharmaceutically acceptable acid addition salts thereof; or a pharmaceutically acceptable solvate thereof, produced by the above processes, may be recovered by conventional methods.

If required mixtures of isomers of the compounds of the invention may be separated into individual stereoisomers by conventional means, for example by the use of an optically active acid as a resolving agent. Suitable optically active acids which maybe used as resolving agents are described in 'Topics in Stereochemistry', Vol. 6, Wiley Interscience, 1971, Allinger, N. L. and Eliel, W. L. Eds.

Alternatively, any enantiomer of a compound of the invention may be obtained by stereospecific synthesis using optically pure starting materials of known configuration.

The absolute configuration of compounds may be determined by conventional X-ray crystallographic techniques.

As previously indicated, the compounds of the present invention have valuable pharmacological properties:

The present invention accordingly provides a compound of formula (I) or a pharmaceutically acceptable acid addition salt thereof, or a pharmaceutically acceptable solvate thereof, for use as an active therapeutic substance.

In one aspect, the present invention provides a compound of formula (I), or a pharmaceutically acceptable acid addition salt thereof, or a pharmaceutically acceptable solvate thereof, for use in the treatment of hyperglycaemia in human or non-human animals.

The present invention further provides a compound of formula (I), or pharmaceutically acceptable acid addition salt thereof, or a pharmaceutically acceptable solvate thereof, for use in the treatment of obesity in human or non-human animals.

A compound of formula (I), or a pharmaceutically acceptable acid addition salt thereof, or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising a compound of formula (I), or a pharmaceutically acceptable acid addition salt thereof, or a pharmaceutically acceptable solvate thereof, and a pharmaceutically acceptable carrier therefor.

As used herein the term "pharmaceutically acceptable" embraces compounds, compositions and ingredients for both human and veterinary use: for example the term "pharmaceutically acceptable salt" embraces a veterinarily acceptable salt.

The composition may, if desired, be in the form of a pack accompanied by written or printed instructions for use.

Usually the pharmaceutical compositions of the present invention will be adapted for oral administration, although compositions for administration by other routes, such as by injection, are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or other conventional adjuvant.

Typical carriers include, for example, microcrystalline cellulose, starch, sodium starch glycollate, polyvinylpyrrolidone, polyvinylpolypyrrolidone, magnesium stearate or sodium lauryl sulphate.

Most suitably the composition will be formulated in unit dose form. Such unit dose will normally contain an amount of the active ingredient in the range of from 0.1 to 1000 mg, more usually 2–100 mg or 0.1 to 500 mg, and more especially 0.1 to 250 mg.

The present invention further provides a method for treating hyperglycaemia in a human or non-human mammal, which comprises administering an effective, non-toxic, amount of a compound of formula (I), or a pharmaceutically acceptable acid addition salt thereof, or a pharmaceutically acceptable solvate thereof, to a hyperglycaemic human or non-human mammal in need thereof.

The present invention further provides a method for treating obesity or for the treatment and/or prophylaxis of atherosclerosis in a human or non-human mammal, which comprises administering an effective, non-toxic, amount of a compound of formula (I), or a pharmaceutically acceptable acid addition salt thereof, or a pharmaceutically acceptable solvate thereof, to a human or non-human mammal in need thereof.

Conveniently, the active ingredient may be administered as a pharmaceutical composition hereinbefore defined, and this forms a particular aspect of the present invention.

In treating hyperglycaemic or obese humans the compound of formula (I), or a pharmaceutically acceptable salt, ester or amide thereof; or a pharmaceutically acceptable solvate thereof, may be taken in doses, such as those described above, one to six times a day in a manner such that the total daily dose for a 70 kg adult will generally be in the range of from 0.1 to 6000 mg, and more usually about 1 to 1500 mg.

The treatment regimens for atherosclerosis are generally as described for hyperglycaemia.

In treating non-human mammals, especially dogs, the active ingredient may be adminstered by mouth, usually once or twice a day and in an amount in the range of from about 0.025 mg/kg to 25 mg/kg, for example 0.1 mg/kg to 20 mg/kg.

In a further aspect the present invention also provides a method for increasing weight gain and/or improving the feed utilisation efficiency and/or increasing lean body mass and/ or decreasing birth mortality rate and increasing post/natal survival rate; of livestock, which method comprises the administration to livestock of an effective non-toxic amount of a compound of formula (I) or a veterinarily acceptable acid addition salt thereof, or a veterinarily acceptable solvate thereof.

Whilst the compounds of formula (I) and the veterinarily acceptable acid addition salts thereof or a veterinarily acceptable solvate thereof, may be administered to any livestock in the abovementioned method, they are particularly suitable for increasing weight gain and/or feed utilisation efficiency and/or lean body mass and/or decreasing birth mortality rate and increasing post-natal survival rate; in poultry, especially turkeys and chickens, cattle, pigs and sheep.

In the preceding method the compounds of formula (I) or veterinarily acceptable acid addition salts thereof will normally be administered orally although non-oral modes of administration, for example injection or implantation, are also envisaged. Suitably the compounds are administered in the feed-stuff or drinking water provided for the livestock. Conveniently these are administered in the feed-stuff at from $10^{-3}$ ppm–500 ppm of total daily fed intake, more usually 0.01 ppm to 250 ppm, suitably less than 100 ppm.

The particular formulations used will of course depend upon the mode of administration but will be those used conventionally in the mode of administration chosen. For administration in feed-stuff the drugs are conveniently formulated as a premix in association with a suitable carrier.

Accordingly, the present invention also provides a veterinarily acceptable premix formulation comprising a compound of formula (I), or a veterinarily acceptable acid addition salt thereof; or a veterinarily acceptable solvate thereof, in association with a veterinarily acceptable carrier therefore.

Suitable carriers are inert conventional agents such as powdered starch. Other conventional feed-stuff premix carriers may also be employed.

No unacceptable toxicological effects are expected when compounds of the invention are administered in accordance with the present invention.

The following Examples illustrate the invention but do not limit it in any way.

PROCEDURE 1

8-Benzyloxy-5-chloroacetylcarbostyril

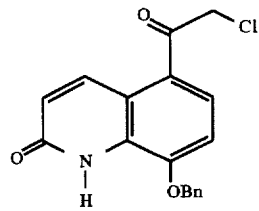

A solution of 5-acetyl-8-benzyloxycarbostyril (1.75 g, 6 mMol) in 1,2-dichloroethane (60 ml)/methanol (40 ml) and benzyltrimethylammonium dichloroiodate (4.2 g, 12 mMol) was heated at 60° C. under an argon atmosphere for 2 hours.

After cooling, the solvent was evaporated and the residue taken up into chloroform (200 ml) washed with sodium metabisulphite solution (100 ml), water (2×75 ml), brine (75 ml), dried and evaporated. Purification by trituration with dichloromethane/diethyl ether gave the title compound as an orange solid; m.p. 201°–203° C.

$^1$H NMR δ (CDCl$_3$) 9.35-9.25 (1H, b, exchanges with D$_2$O), 8.82 (1H, d, J=10 Hz), 7.66 (1H, d, J=8.5 Hz), 7.40 (5H, b), 7.07 (1H, d, J=8.5 Hz), 6.80 (1H, d, J=10 Hz), 5.28 (2H, s) and 4.68 (2H, s) ppm.

PROCEDURE 2

(R)-8-Benzyloxy-5-(2-chloro-1-hydroxyethyl) carbostyril

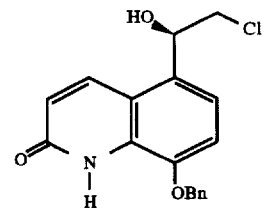

Borane-tetrahydrofuran complex (1M in tetrahydrofuran, 1 ml, 1 mMol) was added dropwise to a solution of (R)-tetrahydro-1-methyl-3,3-diphenyl-1H,3H-pyrrolo [1,2-c][1, 3,2]oxazaborole (0.1 equiv, 30 mg, 0.1 mMol) in tetrahydrofuran (6 ml) at ambient temperature under an argon atmosphere. After 5 minutes, 8-benzyloxy-5-chloroacetylcarbostyril (328 mg, 1 mMol) was added and the reaction mixture was stirred for a further 15 minutes. The reaction mixture was cooled to 5° C. and quenched by the dropwise addition of methanol (2 ml). The quenched reaction mixture was stirred for 15 minutes at 5° C. and for 30 minutes at ambient temperature. The solvent was evaporated and the residue was purified by chromatography on silica gel eluting with 10% methanol in ethyl acetate to afford the title compound as a pale yellow solid; m.p. 148°–149° C.; [α]$_D^{25}$ –9.0° (c=1, methanol).

$^1$H NMR δ ((d$_6$-DMSO) 10.8-10.5 (1H, b, exchanges with D$_2$O), 8.18 (1H, d, J=9.9 Hz), 7.6-7.55(2H, m), 7.4-7.3 (3H, m) 7.19 (2H, b), 6.54 (1H, d, J=9.9 Hz), 5.90 (1H, d, J=4.9 Hz, exchanges with D$_2$O), 5.30 (2H, s), 5.23-5.15 (1H, m) and 3.8-3.6 (2H, m) ppm.

PROCEDURE 3

(R)-8-Benzyloxy-5-oxiranylcarbostyril

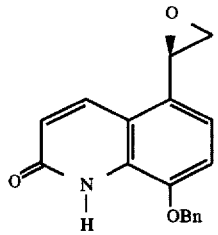

A suspension of (R)-8-benzyloxy-5-(2-chloro-1-hydroxyethyl)carbostyril (130 mg, 0.4 mMol) in acetone (10 ml) containing potassium carbonate (276 mg, 2 mMol) was stirred at 60° C. under an argon atmosphere for 18 hours. After cooling, the suspension was filtered and the filter pad was washed with acetone. The filtrates were combined and evaporated. Purification of the residue by chromatography on silica gel eluting with ethyl acetate gave the title compound as a pale yellow solid; m.p. 146°–150° C.; $[\alpha]_D^{25}$–30° (c=0.91, chloroform).

$^1$H NMR δ (CDCl$_3$) 9.2 (1H, b, exchanges with D$_2$O), 8.10 (1H, d, J=9.9 Hz), 7.42 (5H, b), 7.07 (1H, d, J=8.2 Hz), 7.00 (1H, d, J=8.2 Hz), 6.74 (1H, d, J=9.9 Hz), 5.18 (2H, s), 4.22 (1H, dd, J=3.9, 2.4 Hz), 3.21 (1H, dd, J=5.5, 3.9 Hz) and 2.79 (1H, dd, J=5.5, 2.4 Hz) ppm.

PROCEDURE 4

(R)-3-(3,4-Dihydroxyphenyl)-2-propylamine Hydrobromide

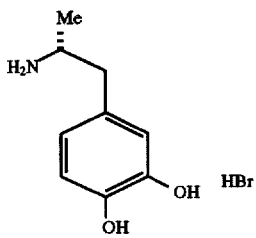

A solution of (R)-3-(3,4-dimethoxyphenyl)-2-propylamine hydrochloride (500 mg, 2.15 mMol) in hydrogen bromide (48%, 5 ml) was stirred at 100° C. under an argon atmosphere for 20 hours. After cooling, the solvent was evaporated and the residue was dried giving the title compound.

$^1$H NMR δ (d$_6$-DMSO/D$_2$O) 6.9-6.4 (3H, m), 3.5-2.4 (3H, m) and 1.3 (3H, d, J=7 Hz) ppm.

PROCEDURE 5

(R)-N-(t-Butyloxycarbonyl)-3-(3,4-dihydroxyphenyl)-2-propylamine

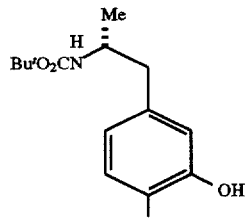

A solution of (R)-3-(3,4-dihydroxyphenyl)-2-propylamine hydrobromide (480 mg, 1.9 mMol) in dimethylformamide (5 ml) containing triethylamine (3 equiv, 586 mg, 5.7 mMol) was stirred at 5° C. under an argon atmosphere for 15 minutes.

Di-tert-butyl dicarbonate (414 mg, 1.9 mMol) was added and the reaction mixture was stirred at 5° C. for 1 hour and then at ambient temperature for 1 hour. The solvent was evaporated. Ethyl acetate (100 ml) and water (50 ml) were added and the organic layer was separated, washed with water (50 ml) and brine (50 ml), dried (MgSO$_4$) and evaporated. Purification of the residue by chromatography on silica gel eluting with 25% ethyl acetate in n-hexane gave the title compound, m.p. 116°–118° C.; $[\alpha]_D^{25}$+2° (c=1, chloroform).

$^1$H NMR δ (CDCl$_3$) 6.76 (1H, d, J=7.9 Hz), 6.70 (1H, d, J=2 Hz), 6.55 (1H, dd, J=7.9, 2 Hz) 6.25-5.90 (2H, b, exchanges with D$_2$O), 4.45 (1H, b, exchanges with D$_2$O), 3.8 (1H, b), 2.75-2.5 (2H, m), 1.43 (9H, s) and 1.07 (3H, d, J=6.6 Hz) ppm.

PROCEDURE 6

(R)-Diethyl-5-[N-(t-butyloxycarbonyl)-2-aminopropyl]-1,3-benzodioxole-2,2-dicarboxylate

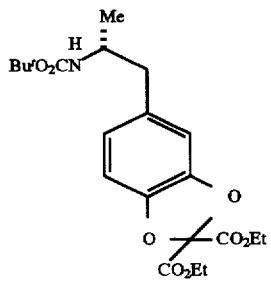

A solution of (R)-N-(t-butyloxycarbonyl)-3-(3,4-dihydroxyphenyl)-2-propylamine (1.07 g, 4 mMol) in acetone (25 ml) containing potassium carbonate (3 equiv, 1.66 g, 12 mMol) was stirred at 60° C. under an argon atmosphere for 1 hour. After cooling to ambient temperature, a solution of diethyl dibromomalonate (1.27 g, 4 mMol) in acetone (7 ml) was added and the reaction was stirred at ambient temperature for 18 hours. The suspension was filtered and the residue was washed with ethyl acetate. The filtrates were combined and evaporated. The residue was partitioned between ethyl acetate (200 ml) and dilute hydrochloric acid (100 ml, pH5). The organic layer was separated, washed with water (2×100 ml) and brine (100 ml), dried (MgSO₄) and evaporated. The residue was purified by column chromatography on silica gel eluting with 25% ethyl acetate in n-hexane giving the title compound as an oil; $[\alpha]_D^{25} -3°$ (c=0.68, chloroform).

¹H NMR δ (CDCl₃) 6.86 (1H, d, J=8 Hz), 6.78 (1H, d, J=1.3 Hz), 6.71 (1H, dd, J=8, 1.3 Hz), 4.41-4.32 (5H, m), 3.8 (1H, b, exchanges with D₂O), 2.76 (1H, dd, J=13.5, 5.6 H₃), 2.60 (1H, dd, J=13.5, 7.2 Hz), 1.43 (9H, s), 1.36-1.31 (6H, m) and 1.07 (3H, d, J=6.6 Hz) ppm.

PROCEDURE 7

(R)-Diethyl-5-(2-aminopropyl)-1,3-benzodioxole-2,2-dicarboxylate Hydrochloride

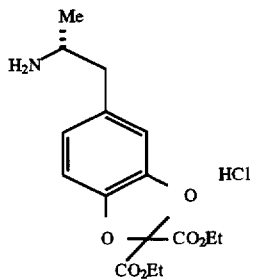

A solution of (R)-diethyl-5-[N-(t-butyloxycarbonyl)-2-aminopropyl]-1,3-benzodioxole-2,2-dicarboxylate (3.0 g, 7 mMol) in ethyl acetate (40 ml) and hydrogen chloride (1M in diethyl ether, 56 ml, 56 mMol) was stirred at ambient temperature under an argon atmosphere for 48 hours. The solvent was evaporated and the residue was dried giving the title compound as a glass.

¹H NMR δ (d₆-DMSO) 8.07 (3H, b, exchanges with D₂O), 7.10-7.06 (2H, m), 6.85 (1H, dd, J=8, 1.4 Hz), 4.33 (4H, q, J=7.1 Hz), 3.5-3.4 (1H, m), 2.93 (1H, dd, J=13.4, 5.8 Hz), 2.66 (1H, d, J=13.5, 8.2 Hz), 1.24 (6H, t, J=7.1 Hz) and 1.12 (3H, d, J=6.3 Hz) ppm.

PROCEDURE 8

(R)-Diethyl-5-(2-aminopropyl)-1,3-benzodioxole-2,2-dicarboxylate

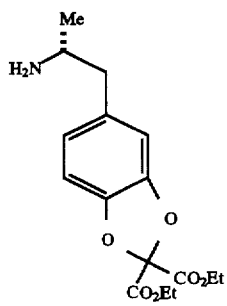

A solution of (R)-diethyl-5-(2-aminopropyl)-1,3-benzodioxole-2,2-dicarboxylate hydrochloride (646 mg, 2 mMol) in dichloromethane (80 ml) was shaken with a saturated solution of sodium hydrogen carbonate (20 ml) for 30 seconds. The organic layer was separated and the aqueous layer was extracted with dichloromethane (2×50 ml). The combined organic extracts were washed with water (50 ml) and brine (50 ml), dried (MgSO₄). The solvent was evaporated giving the title compound which was used immediately in Procedure 9.

PROCEDURE 9

(RR)-Diethyl-5-[2-[2-[5-(8-benzyloxycarbostyryl)]-2-hydroxyethylamino]propyl]-1,3-benzodioxole-2,2-dicarboxylate

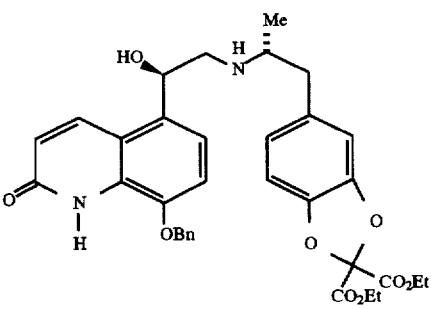

A suspension of (R)-diethyl-5-(2-aminopropyl)-1,3-benzodioxole-2,2-dicarboxylate (2 equiv, 417 mg, 1.3 mMol) and (R)-8-benzyloxy-5-oxiranylcarbostyril (190 mg, 0.65 mMol) in ethanol (10 ml) was heated under reflux under an argon atmosphere for 24 hours. After cooling, the solvent was evaporated. Purification of the residue by chromatography on silica gel eluting with 0–20% methanol in ethyl acetate gave the title compound as a pale orange solid; m.p. 65°-67° C.; $[\alpha]_D^{25} -18°$ (C=0.31, chloroform).

¹H NMR δ (CDCl₃) 9.5-9.0 (1H, b, exchanges with D₂O), 8.10 (1H, d, J=9.9 Hz), 7.41 (5H, b), 7.23 (1H, d, J=8.4 Hz), 7.02 (1H, d, J=8.4 Hz), 6.87 (1H, d, J=8 Hz), 6.79 (1H, d, J=1.2 Hz), 6.71 (1H, dd, J=8, 1.2 Hz), 6.67 (1H, d, J=9.9 Hz), 5.18 (2H, s), 5.06 (1H, dd, J=6.3, 2 Hz), 4.40-4.32 (4H, 2×q, J=7.1 Hz), 3.0-2.93 (2H, m), 2.8-2.6 (3H, m), 2.6-2.4 (2H, b, exchanges with D₂O), 1.37-1.31 (6H, 2×t, J=7.1 Hz) and 1.10 (3H, d, J=6.3 Hz) ppm.

EXAMPLE 1

(RR)-5-[2-[2-[5-(8-Hydroxycarbostyryl)]-2-hydroxyethylamino]propyl]-1,3-benzodioxole-2,2-dicarboxylic Acid

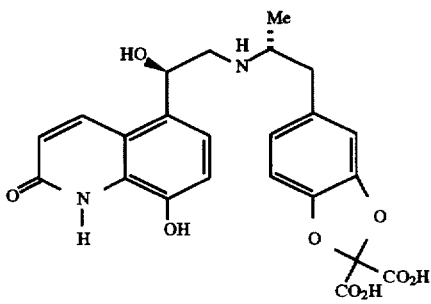

A solution of (RR) diethyl-5-[2-[2-[5-(8-benzyloxycarbostyryl)]-2-hydroxyethylamino]propyl]-1,3-benzodioxole-2,2-dicarboxylate (269 mg, 0.43 mMol) in dioxan (6 ml)/water (2 ml) and lithium hydroxide (1M, 8 equiv, 3.5 ml, 3.5 mMol) was stirred at ambient temperature under an argon atmosphere for 2 hours. The pH of the solution was adjusted to pH7 with 2N hydrochloric acid and the solvent was evaporated.

The residue was dissolved in methanol (25 ml)/water (5 ml), palladium on charcoal (10%, 30 mg) was added and the mixture was hydrogenated at ambient temperature and pressure for 24 hours. The suspension was filtered through a pad of filter aid and the filter pad was washed with methanol (150 ml) and water (20 ml). The filtrates were combined and evaporated giving a dark residue. Purification by chromatography on reverse phase silica eluting with water afforded the title compound as a yellow solid; m.p. >250 °C.; $[\alpha]_D^{25}$ −31° (C=0.51, water).

$^1$H NMR δ (D$_2$O) 8.32 (1H, d, J=9.8 Hz), 7.11 (1H, d, J=8.3 Hz), 6.84-6.76 (3H, m), 6.73 (1H, d, J=9.8 Hz), 6.61 (1H, dd, J=8.3, 1.2 Hz), 5.35 (1H, dd, J=8, 5 Hz), 3.4-3.3 (2H, m), 3.16 (1H, dd, J=12.4, 5 Hz), 3.0-2.77 (2H, m) and 1.23 (3H, d, J=6.3 Hz) ppm.

Pharmacological Data: The activity of the present compounds may be tested by use of the following procedures:

Agonist Activity at Rat $\beta_1$ and $\beta_2$ Adrenoceptors In Vitro $\beta_1$-Adrenoceptor Agonism: Female Sprague-Dawley rats (150–250 g) are killed by a blow to the head and exsanguinated. Spontaneously beating right atria are removed by the method of Broadley and Lumley[1] and mounted on a glass tissue holder. Each tissue is placed in 30 ml organ baths at 37° C. containing Kreb's-Henseleit solution. Each atrium is attached to an isometric transducer by cotton and placed under an initial resting tension of 1 g. Rate recordings from the spontaneous beating atria are obtained from the tension signal using a Lectromed Type 4522 ratemeter. All traces are recorded on a Lectromed M4 chart recorder. β-adrenoceptor agonists are then added to the Krebs medium in a cumulative fashion and the results expressed as a percentage increase in atrial rate.

$\beta_2$-Adrenoceptor Agonism: Rat uterine horns are removed and bisected longitudinally. Each tissue is tied to a glass tissue holder and placed in Krebs-Henseleit solution in a 30 ml organ bath as before. Tissues are placed under a resting tension of 1 g and allowed to equilibrate. Each uterine strip is pre-contracted by the addition of 40 mM K$^+$ to the bath to produced a steady tonic contraction. β-agonists are then added to the bath in a cumulative manner and results expressed as percentage inhibition of contraction.

Agonist EC$_{50}$ (atria) and IC$_{50}$ (uteri) are calculated as the concentration of agonist producing 50% of their maximum increase in atrial rate or uterine relaxation. Relative intrinsic activity expressed as the maximal responses to test agonists relative to isoprenaline (=1.0) in both atria and uteri.

$\beta_3$-Adrenoceptor-Mediated Adenylyl Cyclase Activity: Adenylyl cyclase activity was assayed by the method of Kirkham et. al.[2] by the addition of 40 μl (70–80 μg protein) to the incubation medium of the above CHO cell plasma membranes transfected with the human $\beta_3$-adrenoceptor. cAMP produced over 20 minutes was separated from ATP by the method of Salomon et al.[3] Agonist EC$_{50}$ values and intrinsic activities were expressed as the concentration of agonist producing 50% activation of adenylyl cyclase and the maximum response produced by each agonist relative to that produced by (−) isoprenaline respectively.

References

1. K. J. Broadley & P. Lumley (1977) Br. J. Pharmacol. 59. 51
2. D. Kirkham et. al., Biochem. J., 1992, 284, 301.
3. Y. Salomon et al., Anal. Biochem., 1974, 58, 541.

We claim:

1. A compound of formula (I):

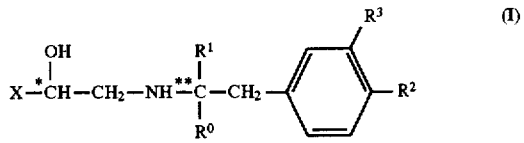

or a pharmaceutically acceptable salt thereof, or a pharmaceutically acceptable solvate thereof, wherein, X represents a moiety of formula (a):

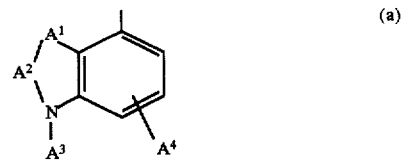

in which A$^1$ represents —CH=CH=; A$^2$ represents an oxo or a thioxo group; A$^3$ represents H or an alkylcarbonyl group; and A$^4$ represents hydroxy or NR$^r$R$^t$ wherein R$^s$ and R$^t$ each independently represents H or alkyl;

R$^0$ and R$^1$ each independently represents hydrogen or an alkyl group;

R$^2$ represents OCH$_2$CO$_2$H, or an ester or amide thereof, or R$^2$ represents a moiety of formula (b):

wherein R$^4$ and R$^5$ each independently represent hydrogen, alkyl, hydroxyalkyl, cycloalkyl or R$^4$ together with R$^5$ represents (CH$_2$)$_m$ wherein m is 2, 3 or 4; and R$^3$ represents hydrogen, halogen, alkyl or alkoxy or R$^3$ together with R$^2$ represents a moiety of formula (c):

or an ester or amide thereof, wherein R represents hydrogen, alkyl, hydroxymethyl or a moiety of formula (CH$_2$)$_n$CO$_2$H, wherein n is zero or an integer 1, 2 or 3, or an ester or amide thereof.

2. A compound according to claim 1, wherein A$^1$ is —CH=CH—.

3. A compound according to claim 1, wherein A$^2$ is oxo.

4. A compound according to claim 1, wherein A$^3$ is H.

5. A compound according to claim 1, wherein A$^4$ is OH, substituted at the 4-position relative to the bond linking X to the CHOH carbon atom.

6. A compound according to claim 5, wherein R$^0$ is hydrogen.

7. A compound according to claim 5, wherein R$^1$ is an alkyl group.

8. A compound according to claim 1, wherein R$^2$ together with R$^3$ represents a moiety of formula (c).

9. A compound according to claim 1, being: (RR)-5-[2-[2-[5-(8-hydroxycarbostyryl)]-2-hydroxyethylamino] propyl]-1,3-benzodioxole-2,2-dicarboxylic acid or a pharmaceutically acceptable salt thereof, or a pharmaceutically acceptable solvate thereof.

10. A compound according to claim 1, wherein with reference to formula (I), the asymmetric carbon atom corresponding to that indicated by a single asterisk (*) is in the S-configuration and the asymmetric carbon atom corresponding to that indicated by two asterisks (**) is in the R-configuration.

11. A process for the preparation of a compound according to claim 1, or a salt thereof or a solvate thereof, which process comprises reacting a compound of formula (II):

wherein $X^1$ represents X as defined according to claim 1 or a protected form thereof, with a compound of formula (III):

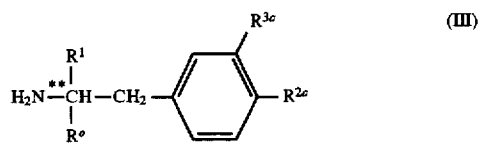

wherein $R^0$, $R^1$ are as defined in claim 1, $R^{2a}$ represents $R^2$ as defined in claim 1 or a protected form thereof and $R^{3a}$ represents $R^3$ as defined in claim 1 or a protected form thereof; and thereafter, if necessary, carrying out one or more of the following optional steps:

(i) converting one compound of claim 1 to another compound of claim 1; and (ii) removing any protecting group; and (iii) preparing a pharmaceutically acceptable salt thereof of a compound of claim 1 or a pharmaceutically acceptable solvate thereof.

12. A pharmaceutical composition comprising a compound of claim 1, or a pharmaceutically acceptable salt thereof; or a pharmaceutically acceptable solvate thereof, and a pharmaceutically acceptable carrier therefor.

13. A method for treating hyperglycaemia, obesity, or hyperinsulinaemia in a human or non-human mammal, which comprises administering an effective, non-toxic, amount of a compound of claim 1, or a pharmaceutically acceptable salt thereof; or a pharmaceutically acceptable solvate thereof, to the human or non-human mammal in need thereof.

* * * * *